US012714322B2

(12) United States Patent
Tang et al.

(10) Patent No.: US 12,714,322 B2
(45) Date of Patent: Aug. 25, 2026

(54) OPTICAL MODULE

(71) Applicant: Advanced Semiconductor Engineering, Inc., Kaohsiung (TW)

(72) Inventors: Shih-Chieh Tang, Kaohsiung (TW); Hsun-Wei Chan, Kaohsiung (TW); Hsin-Ying Ho, Kaohsiung (TW)

(73) Assignee: Advanced Semiconductor Engineering, Inc., Kaohsiung (TW)

( * ) Notice: Subject to any disclaimer, the term of this patent is extended or adjusted under 35 U.S.C. 154(b) by 550 days.

(21) Appl. No.: 18/096,361

(22) Filed: Jan. 12, 2023

(65) Prior Publication Data

US 2024/0237907 A1 Jul. 18, 2024

(51) Int. Cl.

| | |
|---|---|
| *A61B 5/024* | (2006.01) |
| *A61B 5/1455* | (2006.01) |
| *A61B 5/282* | (2021.01) |
| *A61B 5/33* | (2021.01) |

(52) U.S. Cl.
CPC ...... *A61B 5/02427* (2013.01); *A61B 5/14551* (2013.01); *A61B 5/282* (2021.01); *A61B 5/33* (2021.01); *A61B 2562/06* (2013.01)

(58) Field of Classification Search
CPC ............ A61B 5/02427; A61B 5/02416; A61B 5/14552
See application file for complete search history.

(56) References Cited

U.S. PATENT DOCUMENTS

| | | | | |
|---|---|---|---|---|
| 10,910,507 | B2 | 2/2021 | Huang et al. | |
| 2014/0364707 | A1* | 12/2014 | Kintz | A61B 5/1459 600/310 |
| 2017/0127975 | A1* | 5/2017 | Bozkurt | A01K 29/005 |
| 2020/0315473 | A1* | 10/2020 | Peterson | A61B 5/681 |
| 2021/0393154 | A1* | 12/2021 | Gelissen | A61B 5/02416 |

* cited by examiner

*Primary Examiner* — Tammie K Marlen
(74) *Attorney, Agent, or Firm* — Foley and Lardner LLP

(57) ABSTRACT

An optical module is disclosed. The optical module includes a carrier, an optical device disposed over the carrier, and a sensing surface facing away from the carrier. The sensing surface includes a transmissive region and a non-transmissive region adjacent to the transmissive region.

19 Claims, 12 Drawing Sheets

OPTICAL MODULE

BACKGROUND

1. Field of the Disclosure

The present disclosure relates to an optical module.

2. Description of the Related Art

Photoplethysmography (PPG) can be used to monitor changes in blood volume, pulse rate, oxygen saturation, blood pressure, blood vessel stiffness, etc. Conventionally, a PPG sensor includes a cover or a housing for accommodating an emitter and a receiver. A gap may exist between the emitter and the cover, and mediums having different refractive indices may cause refractive index mismatch, which may in turn decrease the external quantum efficiency (EQE) of the emitter. In addition, the gap creates the need to achieve water resistance to prevent reliability issues due to water ingress.

SUMMARY

In some arrangements, an optical module includes a carrier, an optical device disposed over the carrier, and a sensing surface facing away from the carrier. The sensing surface includes a transmissive region and a non-transmissive region adjacent to the transmissive region.

In some arrangements, an optical module includes a carrier and an optical device disposed over the carrier and configured to receive an optical signal external to the optical module. The optical module also includes a first electrode disposed over the carrier and configured to detect an electrical signal external to the optical module. The optical device and the first electrode are disposed at a same side of the carrier.

In some arrangements, an optical module includes a carrier, an optical device disposed over the carrier, and a sensing surface facing away from the carrier. The sensing surface includes a conductive region and a non-conductive region adjacent to the conductive region.

BRIEF DESCRIPTION OF THE DRAWINGS

Aspects of some arrangements of the present disclosure are readily understood from the following detailed description when read with the accompanying figures. It is noted that various structures may not be drawn to scale, and dimensions of the various structures may be arbitrarily increased or reduced for clarity of discussion.

DETAILED DESCRIPTION

Figure 1A:
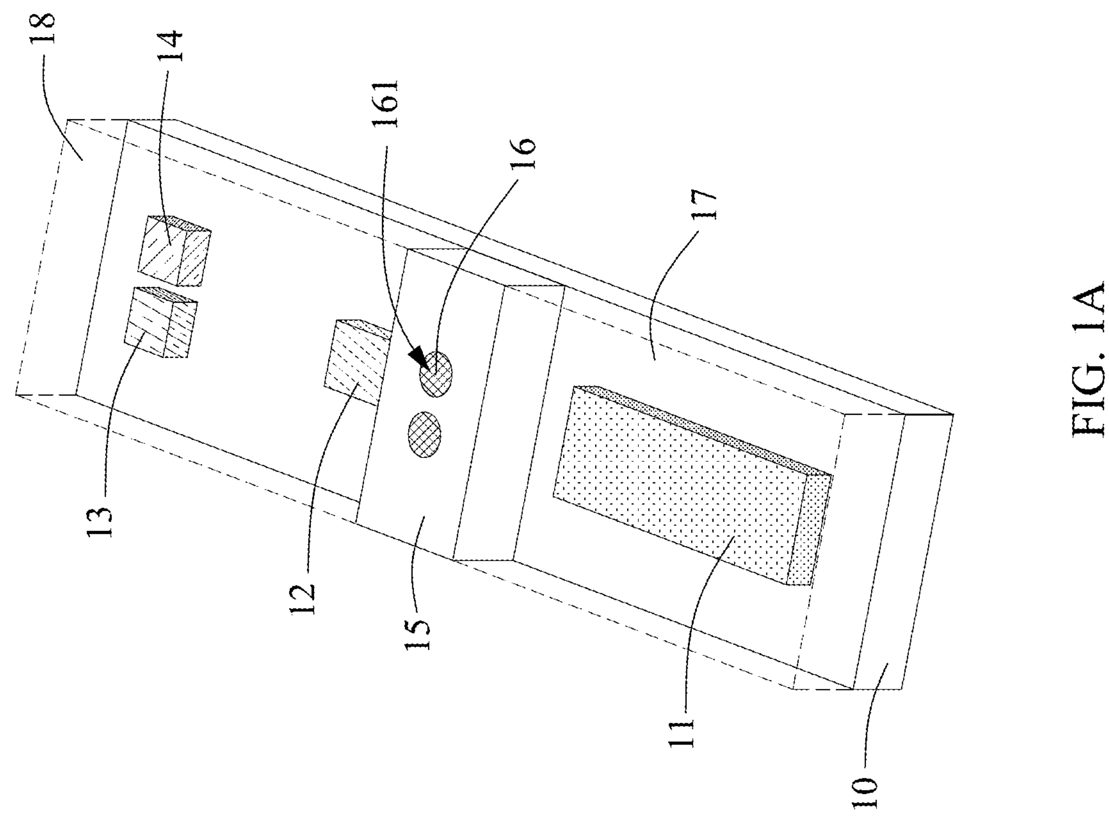
FIG. 1A illustrates a perspective view of an example of an optical module according to some arrangements of the present disclosure.

Common reference numerals are used throughout the drawings and the detailed description to indicate the same or similar components. Arrangements of the present disclosure will be readily understood from the following detailed description taken in conjunction with the accompanying drawings.

The following disclosure provides many different arrangements, or examples, for implementing different features of the provided subject matter. Specific examples of components and arrangements are described below to explain certain aspects of the present disclosure. These are, of course, merely examples and are not intended to be limiting. For example, the formation of a first feature over or on a second feature in the description that follows may include arrangements in which the first and second features are formed or disposed in direct contact, and may also include arrangements in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various arrangements and/or configurations discussed.

Figure 1B:
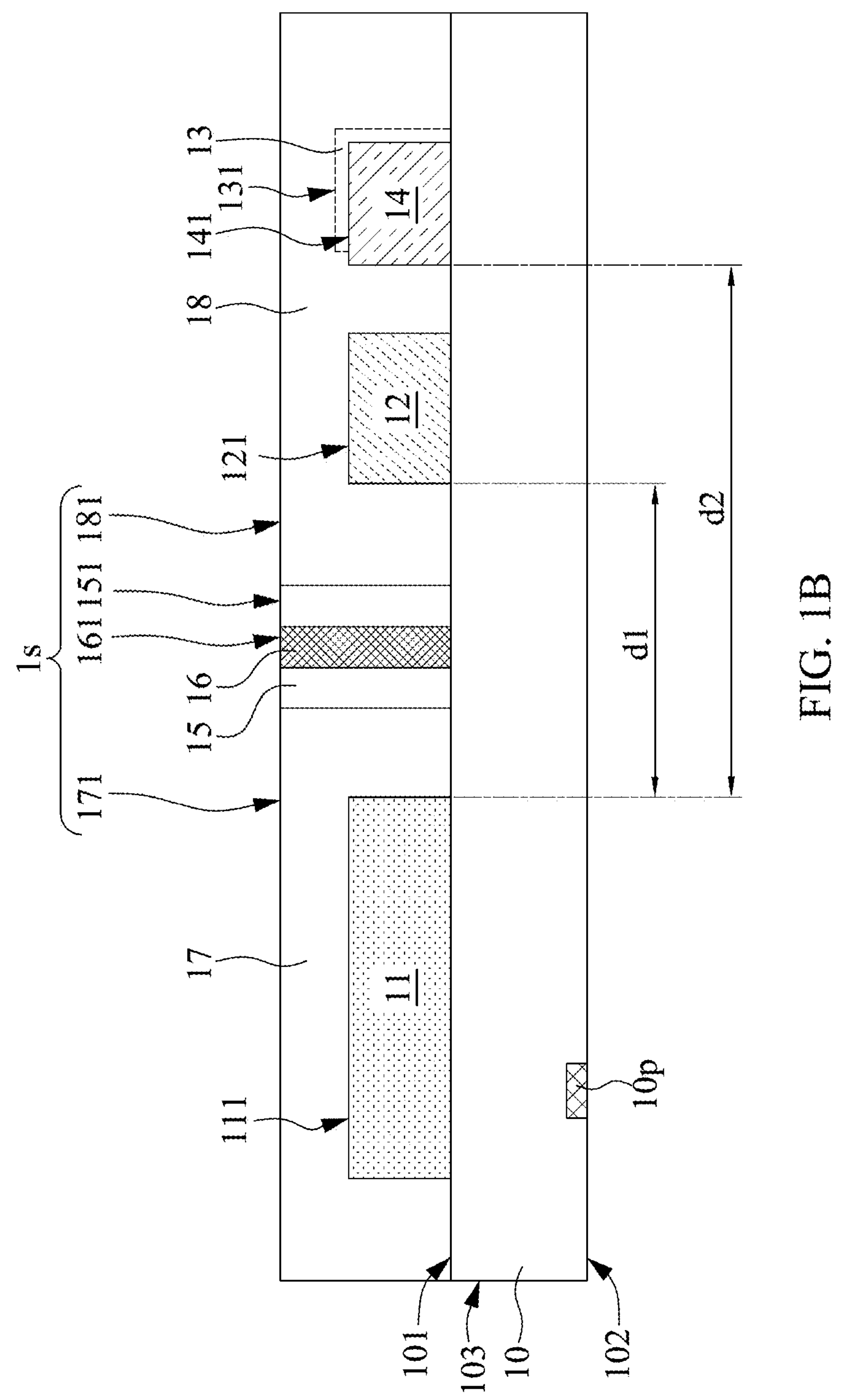
FIG. 1B illustrates a cross-sectional view of an example of an optical module according to some arrangements of the present disclosure.

FIG. 1A illustrates a perspective view of an example of an optical module 1 according to some arrangements of the present disclosure. FIG. 1B illustrates a cross-sectional view of an example of the optical module 1 according to some arrangements of the present disclosure.

The optical module 1 may include or be a part of an electronic component or an electronic module, such as a system-in-package (SiP) module. In some arrangements, the optical module 1 may include or be a part of a wearable device, such as a smartwatch, a smart band, or another smart wearable device. For example, the optical module 1 may be configured to be worn by and/or attached to an object or a target. The object may include a human or an animal. In some arrangements, the optical module 1 may include or be a part of a portable electronic device, such as a laptop, a cellular telephone, a tablet, a notebook, a camera, a radio, etc. Configuration or application of the optical module 1 in the figures is for illustrative purposes only, and not intended to limit the present disclosure.

The optical module 1 may include or be a part of a monitoring device or a detecting device. In some arrangements, the optical module 1 may be a piece of equipment that detects signals or pieces of information, such as biological signals, physiological signals, motions (e.g., body motions of the human or animal), and/or environmental information in a vicinity of an object or a target. In some arrangements, the optical module 1 may include a photoplethysmography (PPG) that can be used to monitor changes in blood volume, pulse rate, oxygen saturation, blood pressure, blood vessel stiffness, etc.

In some arrangements, the optical module 1 may perform data communication with a base station or a terminal device (such as a mobile phone) in a wireless communications manner, such as via radio frequency identification technology or short-range wireless communications technology. In some arrangements, the optical module 1 may be used in combination with a detection device (such as a sensor), an electronic device (such as a signal processing device) and/or other corresponding external devices for further processing acquired signals.

Referring to FIG. 1A and FIG. 1B, the optical module 1 may include a carrier 10, an optical receiver 11, optical emitters 12, 13, 14, a light blocking structure 15, one or more conductive elements 16, and encapsulants 17, 18.

The carrier 10 may include a substrate. The carrier 10 may include a printed circuit board (PCB), such as a paper-based copper foil laminate, a composite copper foil laminate, or a polymer-impregnated glass-fiber-based copper foil laminate. In some arrangements, the carrier 10 may include an interconnection structure, such as a redistribution layer (RDL) or a grounding element.

The carrier 10 may include a surface 101, a surface 102 opposite to the surface 101, and a lateral surface 103 extending between the surface 101 and the surface 102. The carrier 10 may include one or more conductive pads in proximity to, adjacent to, or embedded in and exposed from the surface 101 and/or the surface 102. The carrier 10 may include a solder resist (not shown) on the surface 101 and/or the surface 102 to fully expose or to expose at least a portion of the conductive pads for electrical connections. In some arrangements, a connector (not shown) may be disposed over or on the surface 102 to provide an electrical connection between the optical module 1 and an external component (such as a PCB). In some arrangements, the connector may include one or more solder balls or solder bumps, such as a controlled collapse chip connection (C4) bump, a ball grid array (BGA) or a land grid array (LGA).

The optical receiver 11 may be disposed over or on the surface 101 of the carrier 10. The optical receiver 11 may be electrically connected to the carrier 10 through solder bonding, Cu-to-Cu bonding, wire bonding, or hybrid bonding.

The optical receiver 11 may include a photo-detector, a photo-sensor, a photodiode (PD), a charge-coupled device (CCD), a photomultiplier tube, a camera, a spectrometer, or another light-sensitive electronic device. The optical receiver 11 may be configured to receive light (or EM radiation in the ultraviolet, visible, and/or infrared spectral regions) and generate electrical signals (e.g., an electrical current). The optical receiver 11 may be configured to receive light from outside of the optical module 1. For example, the optical receiver 11 may convert light energy in the form of photons to an electric current. In some arrangements, the electrical signals from the optical receiver 11 may be further processed (by, for example, an electronic component communicated or collectively used with the optical module 1) to determine a biological parameter of the object or the target.

The optical receiver 11 may include a surface 111 facing away from the carrier 10. The surface 111 may include an active surface, an active region, or a light receiving region. Light may be received by the light receiving region.

The optical emitters 12, 13, and 14 may each be disposed over or on the surface 101 of the carrier 10. The optical emitters 12, 13, and 14 may each be electrically connected to the carrier 10 through solder bonding, Cu-to-Cu bonding, wire bonding, or hybrid bonding.

The optical emitters 12, 13, and 14 may each include a light emitting diode (LED), a laser diode (such as vertical cavity surface-emitting laser (VCSEL)), a lamp, a laser, any other suitable light source, or a combination thereof. The optical emitters 12, 13, and 14 may each be configured to generate or emit light or EM radiation in the ultraviolet, visible, and/or infrared spectral regions.

The optical emitters 12, 13, and 14 may be configured to emit light of different wavelengths (or frequencies, or bandwidths). For example, the optical emitter 12 may include a light source that emits visible light of one or more wavelengths (or frequencies, or bandwidths), such as green light. For example, the optical emitter 13 may include a light source that emits visible light of one or more wavelengths (or frequencies, or bandwidths), such as red light. For example, the optical emitter 14 may include a light source that emits invisible light of one or more wavelengths (or frequencies, or bandwidths), such as infrared (IR) light. The optical module 1 may include any number of light sources, such as an array of pixels.

The optical emitter 12 may include a surface 121 facing away from the carrier 10. The optical emitter 13 may include a surface 131 facing away from the carrier 10. The optical emitter 14 may include a surface 141 facing away from the carrier 10. The surfaces 121, 131, and 141 may each include an active surface, an active region, or a light emitting region. Light may be emitted from the surfaces 121, 131, and 141. Light may be emitted outside of the optical module 1. Light may be emitted externally.

In some arrangements, the light from the optical emitters 12, 13, and/or 14 may be received by (or may radiate) an object or a target. The object or the target may scatter or reflect at least a portion of the light and the scattered or reflected light may return toward the optical module 1 and be received by the optical receiver 11.

As stated, the optical receiver 11 may be configured to receive light and generate electrical signals. The electrical signals may be related to one or more properties of the light, such as luminous flux (or luminous power or brightness), luminous intensity, propagation direction, wavelength (or frequency, or bandwidth), polarization state, etc.

In some arrangements, the optical receiver 11 and the optical emitters 12, 13, 14 may collaboratively provide an optical measurement function or a light-based sensing function, such as a photoplethysmography (PPG) measurement, for the optical module 1. For example, the optical receiver 11 and the optical emitters 12, 13, 14 may collaboratively function as a PPG sensor. For example, the electrical signals from the optical receiver 11 may be further processed (by, for example, an electronic component communicated or collectively used with the optical module 1) to determine a biological parameter of the object or the target, such as changes in blood volume, pulse rate, oxygen saturation, blood pressure, blood vessel stiffness, etc.

In some arrangements, the light from the optical emitters 12, 13, and 14 may be used to monitor different signals or pieces of information. For example, the light from the optical emitter 12 may be used to monitor pulse rate. For example, the light from the optical emitter 13 and the optical emitter 14 may be used to monitor oxygen saturation.

In some arrangements, the optical emitters 12, 13, and 14 may be configured to emit light during different time intervals. For example, the optical emitters 12, 13, and 14 may be configured to emit light in a time division manner. Therefore, the reflected light of the light emitted from the optical emitters 12, 13, and 14 can be received by the same light receiving region of the optical receiver 11 and monitored during different time intervals.

For example, the optical emitter 12 may emit light (such as a first light or green light) during a first-time interval and the optical receiver 11 may receive the reflected light of the first light during the first-time interval to monitor the first light. In some arrangements, the optical receiver 11 and the optical emitter 12 may be collaboratively configured to monitor a biological parameter (such as pulse rate) of an object or a target during the first-time interval.

For example, the optical emitter 13 may emit light (such as a second light or red light) during a second-time interval and the optical receiver 11 may receive the reflected light of the second light during the second-time interval to monitor the second light. The optical emitter 14 may emit light (such as a third light or IR light) during a third-time interval and the optical receiver 11 may receive the reflected light of the third light during the third-time interval to monitor the third light. In some arrangements, the optical receiver 11, the optical emitter 13, and the optical emitter 14 may be collaboratively configured to monitor a biological parameter (such as oxygen saturation) of an object or a target during the second-time interval and the third-time interval.

In some arrangements, the optical receiver 11 may include multiple light receiving regions, and the reflected light of the light emitted from the optical emitters 12, 13, and 14 can be received by the optical receiver 11 simultaneously. For example, the optical receiver 11 may include a light receiving region for receiving the light (such as a first light or green light) from the optical emitter 12, a light receiving region for receiving the light (such as a second light or red light) from the optical emitter 13, and a light receiving region for receiving the light (such as a third light or IR light) from the optical emitter 14. Therefore, the first-time interval, the second-time interval, and the third-time interval may be at least partially overlapped.

For example, the optical emitters 12, 13, and 14 may emit light simultaneously. For example, at least three light beams may be emitted from the optical emitters 12, 13, and 14 simultaneously. For example, the optical receiver 11 may receive at least three light beams simultaneously. For example, at least three light beams may be monitored simultaneously. The number of the light receiving regions may be adjusted according to design requirements and are not intended to limit the present disclosure.

The optical module 1 may include three transmitters (i.e., TX or the optical emitters 12, 13, and 14) and one receiver (i.e., RX or the optical receiver 11). The relative positions and the number of the transmitter and the receiver may be adjusted according to design requirements and are not intended to limit the present disclosure.

Figure 2:
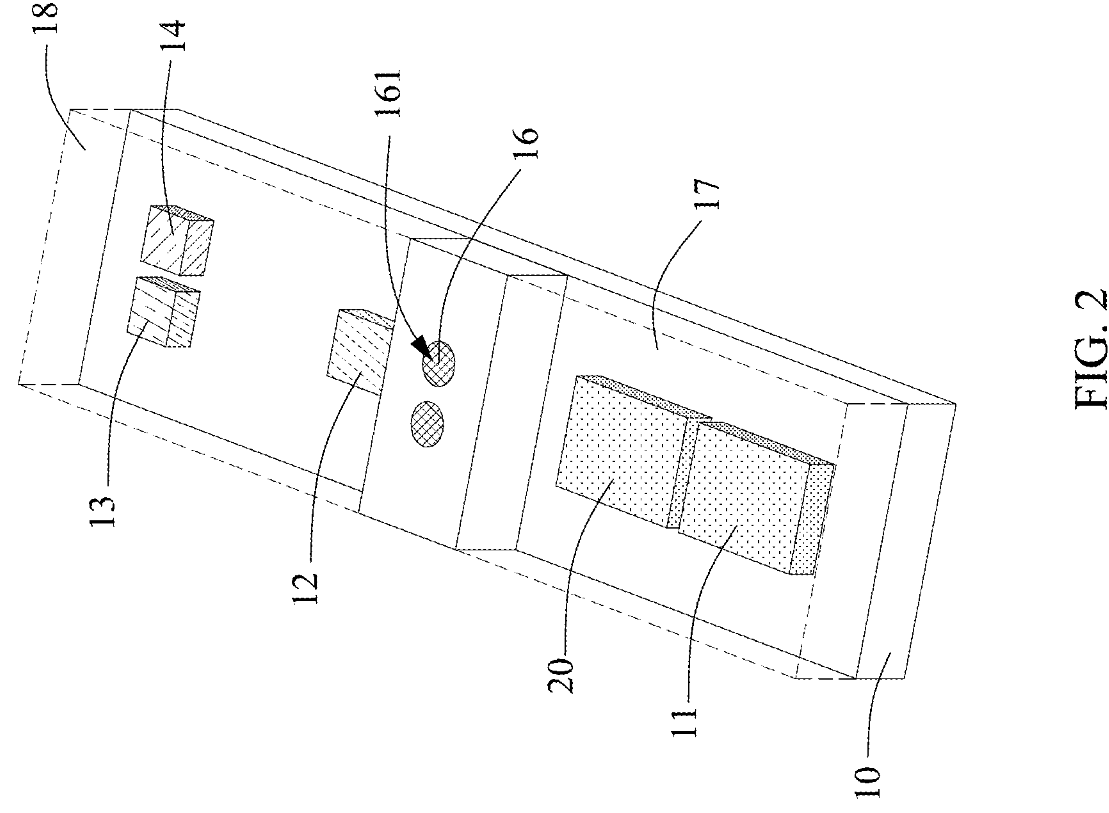
FIG. 2 illustrates a perspective view of an example of an optical module according to some arrangements of the present disclosure.

In some arrangements, as shown in FIG. 2, the optical emitter 12 may be disposed closer to the optical receiver 11 than the optical emitter 13 (or the optical emitter 14). The distance "d1" between the optical receiver 11 and the optical emitter 12 may be shorter than the distance "d2" between the optical receiver 11 and the optical emitter 13 (or the optical emitter 14). In some arrangements, the optical emitter 13 and the optical emitter 14 may be disposed at substantially the same distance (i.e., the distance "d2" in FIG. 2) from the optical receiver 11. In some arrangements, since the light emitted from the optical emitter 12 is relatively weaker than the light emitted from the optical emitter 13 (or the optical emitter 14), the sensitivity of the optical receiver 11 can be enhanced by disposing the optical emitter 12 closer to the optical receiver 11.

The light blocking structure 15 may be disposed over or on the surface 101 of the carrier 10. The light blocking structure 15 may be disposed between the optical receiver 11 and one of the optical emitters 12, 13, and 14.

The light blocking structure 15 may be non-transmissive to the light emitted from the optical emitters 12, 13, and/or 14. In some arrangements, the light blocking structure 15 may be configured to transmit almost no light, and therefore reflect, scatter, or absorb all of it. The light blocking structure 15 may include an opaque material, such as opaque epoxy (e.g., black epoxy), opaque resin, ink, carbon black, photoresist, a metal layer, or other non-transparent materials. In some arrangements, the light blocking structure 15 may include a shielding layer.

In some arrangements, the light blocking structure 15 may include a non-conductive material. For example, the light blocking structure 15 may include a non-conductive opaque material. However, in some arrangements, the light blocking structure 15 may include a conductive material. For example, the light blocking structure 15 may include a conductive opaque material.

In some arrangements, the light blocking structure 15 may be configured to block, reflect, scatter, or absorb light emitted from the optical emitters 12, 13, and/or 14. The light blocking structure 15 may be configured to avoid crosstalk between the transmitters (i.e., TX or the optical emitters 12, 13, and 14) and the receiver (i.e., RX or the optical receiver 11). For example, the light blocking structure 15 may be configured to isolate the transmitters from the receiver. For example, the light blocking structure 15 may be configured to prevent the light radiated from the transmitter(s) directly received by the receiver. For example, the light blocking structure 15 may be configured to reduce light leakage.

The conductive element 16 may be disposed over or on the surface 101 of the carrier 10. The conductive element 16 and an optical component (e.g., the optical receiver 11 and the optical emitters 12, 13, 14) may be disposed at the same side of the carrier 10. The conductive element 16 may be electrically connected to the carrier 10. The conductive element 16 may be partially covered or encapsulated by the light blocking structure 15. The conductive element 16 may penetrate the light blocking structure 15. A surface (or a top surface) 161 of the conductive element 16 may be at least partially exposed from the light blocking structure 15. The conductive element 16 may extend between the surface 151 of the light blocking structure 15 and a surface of the light blocking structure 15 opposite to the surface 151. The surface 161 of the conductive element 16 may form a circle from the top view. However, in some arrangements, the surface 161 of the conductive element 16 may form an oval, a square, a rectangle, a triangle, or other shapes.

In some arrangements, the conductive element 16 may include a conductive pillar, a conductive pad, a conductive via, a conductive wire, another feasible connector, or a combination thereof. In some arrangements, one or more of the conductive elements 16 may taper toward the carrier 10.

In some arrangements, one or more of the conductive elements 16 may taper away from the carrier 10. In some arrangements, one or more of the conductive elements 16 may have a constant width.

The conductive element 16 may include copper (Cu) or other conductive materials, such as aluminum (Al), chromium (Cr), tin (Sn), gold (Au), silver (Ag), nickel (Ni), stainless steel, another metal, or a mixture, an alloy, or other combinations of two or more thereof.

In some arrangements, the conductive element 16 may have a relatively lower impedance than the light blocking structure 15. In some arrangements, the conductive element 16 may have a relatively higher electrical conductivity than the light blocking structure 15.

In some arrangements, the conductive element 16 may function as a sensing pad or an electrode. For example, the surface 161 of the conductive element 16 may be configured to detect or collect one or more electrical signals or pieces of information external to the optical module 1. For example, the surface 161 of the conductive element 16 may be configured to detect or collect one or more electrical signals or pieces of information associated with an object or a target.

In some arrangements, the electrical signals detected by the conductive element 16 may include an electrical voltage. In some arrangements, the electrical signals detected by the conductive element 16 may be further processed (by, for example, an electronic component communicated or collectively used with the optical module 1) to determine a biological parameter of the object or the target, such as a pulse travel time (PTT), an electroencephalogram (EEG), electrocardiogram (ECG), electromyogram (EMG), electrooculogram (EOG), galvanic skin response (GSR), sweat composition, pH, heart rate variability (HRV), or other biologically-relevant information associated with the object or the target.

In some arrangements, the conductive element 16 may be configured to provide an electrical measurement function or an electrical sensing function, such as an ECG function, for the optical module 1. For example, a 2-lead ECG function may be provided when an object (such as a user) of the optical module 1 contacts the surface 161 of the conductive element 16 (or a first electrode) and a conductive element 10*p* distinct from the conductive element 16.

In some arrangements, the conductive element 10*p* may be disposed or provided over or on the surface 102 of the carrier 10. In some arrangements, the conductive element 10*p* may include a sensing pad, an electrode, or a connector. The conductive element 10*p* may be disposed over a surface to make it easier for the user to place different body parts thereon. As another example, a 3-lead ECG function may be provided when the user of the optical module 1 contacts first and second electrodes that receive electrical signals from the user, and a third electrode that grounds the user to the optical module 1.

In both the 2-lead and 3-lead ECG embodiments, the user may press the first electrode against a first part of their body and press the second electrode against a second part of their body. The third electrode may be pressed against the first or second body part, depending on where it is located on the optical module 1. In some arrangements, the conductive element 16 may be configured for pressing along a direction substantially perpendicular to the surface 101 and/or the surface 102 of the carrier 10. For example, the conductive element 16 may function as a button. For example, the conductive element 16 may have resilience such that the conductive element 16 may spring back into shape after being pressed along a direction substantially perpendicular to the surface 101 and/or the surface 102 of the carrier 10.

In some arrangements, the sensing pad or electrode (such as the conductive element 16 and the conductive element 10*p*) for providing an electrical measurement function (such as an ECG function) for the optical module 1 may be disposed at a same side of the carrier 10. In some arrangements, the sensing pad or electrode may be disposed at different sides of the carrier 10.

In some arrangements where the light blocking structure 15 is conductive, the entirety of the light blocking structure 15 may be an electrode. The conductive element 16 may be configured to enhance, accelerate, or facilitate the signal transmission between a sensing surface 1*s* of the optical module 1 and the carrier 10.

The encapsulant 17 may be disposed over or on the surface 101 of the carrier 10 to cover or encapsulate the optical receiver 11. The encapsulant 18 may be disposed over or on the surface 101 of the carrier 10 to cover or encapsulate the optical emitters 12, 13, and 14. The encapsulant 18 may be disposed adjacent to the optical receiver 11. The encapsulants 17 and 18 may each include a light transmissive material, such as clear glass, clear plastic, clear gel, clear resin, clear epoxy, sapphire, or other transparent materials.

In some arrangements, the light emitted from the optical emitters 12, 13, and/or 14 may be optically coupled to the encapsulant 18. "Optically coupled" is defined herein as including the coupling, attaching or adhering two or more regions or layers such that the intensity of light passing from one region to the other is not substantially reduced due to Fresnel interfacial reflection losses due to differences in refractive indices between the regions.

In some arrangements, the light emitted from the optical emitters 12, 13, and/or 14 may be directly optically coupled to the encapsulant 18. "Directly optically coupling" a first and second region or material refers to the optical coupling of the regions or materials wherein light travelling through the first region can directly pass into the second region without passing through an intermediate region.

In some arrangements, a surface (or a top surface) 151 of the light blocking structure 15, the surface 161 of the conductive element 16, a surface (or a top surface) 171 of the encapsulant 17, and a surface (or a top surface) 181 of the encapsulant 18 may collectively define the sensing surface Is of the optical module 1. In some arrangements, the surface 151 of the light blocking structure 15, the surface 161 of the conductive element 16, the surface 171 of the encapsulant 17, and the surface 181 of the encapsulant 18 may be substantially coplanar.

In some arrangements, the sensing surface Is may face away from the carrier 10. In some arrangements, the sensing surface Is of the optical module 1 may be configured to face or contact an object (such as a user) of the optical module 1. The sensing surface Is of the optical module 1 may include a transmissive region (such as the surface 171 of the encapsulant 17 and/or the surface 181 of the encapsulant 18) and a non-transmissive region (such as the surface 151 of the light blocking structure 15 and/or the surface 161 of the conductive element 16) adjacent to the transmissive region. The transmissive region may be transmissive to the light emitted from the optical emitters 12, 13, and/or 14 and the non-transmissive region may be non-transmissive to the light emitted from the optical emitters 12, 13, and/or 14.

In some arrangements, the non-transmissive region (such as a combination of the surface 151 of the light blocking structure 15 and the surface 161 of the conductive element 16) may be disposed between two transmissive regions (such as the surface 171 of the encapsulant 17 and the surface 181 of the encapsulant 18).

In some arrangements, the non-transmissive region may be configured to be contacted by an object and receive an electrical signal from the object. For example, the surface 161 of the conductive element 16 may be configured to detect or collect one or more electrical signals or pieces of information associated with the object. In some arrangements, the electrical signals detected by the conductive element 16 may be further processed (by, for example, an electronic component communicated or collectively used with the optical module 1) to determine a biological parameter of the object, such as ECG.

In some arrangements, the transmissive region may be configured to face the object and receive an optical signal from the object. For example, the optical receiver 11 may be configured to receive light and generate electrical signals. The optical receiver 11 and the optical emitters 12, 13, 14 may collaboratively provide an optical measurement function or a light-based sensing function, such as PPG measurement, for the optical module 1.

In some arrangements, the sensing surface Is of the optical module 1 may include a conductive region (such as the surface 151 of the light blocking structure 15 and/or the surface 161 of the conductive element 16) and a non-conductive region (such as the surface 171 of the encapsulant 17 and/or the surface 181 of the encapsulant 18). In some arrangements, the conductive region (such as a combination of the surface 151 of the light blocking structure 15 and the surface 161 of the conductive element 16, if the light blocking structure 15 conductive) may be disposed between two non-conductive regions (such as the surface 171 of the encapsulant 17 and the surface 181 of the encapsulant 18).

In a comparative arrangement, a PPG sensor may include a cover or a housing for accommodating an emitter and a receiver. A gap may exist between the emitter and the cover, and mediums having different refractive indices may cause refractive index mismatch, which may in turn decrease external quantum efficiency (EQE) of the emitter. In addition, the gap creates the need to achieve water resistance to prevent reliability issues due to water ingress.

According to some arrangements of the present disclosure, by using the encapsulants 17 and 18, the refractive index mismatch may be reduced, the EQE can be increased, and the sensitivity of the optical module 1 can be enhanced in comparison with using a cover. In addition, the size of the optical module 1 can be further reduced and the reliability issue due to water ingress can be solved. Furthermore, the conductive element 16 can provide an ECG function for the optical module 1 to improve the usability of the optical module 1. For example, the optical module 1 can be a PPG sensor having a 2-lead ECG function or a 3-lead ECG function.

FIG. 2 illustrates a perspective view of an example of an optical module 2 according to some arrangements of the present disclosure. The optical module 2 is similar to the optical module 1 in FIG. 1A except for the differences described as follows.

The optical module 2 includes an optical receiver 20. The optical receiver 20 may be similar to the optical receiver 11 of FIG. 1A. Therefore, some details of the optical receiver 20 may correspond to the paragraphs described above for FIG. 1A, and a description thereof is not repeated hereinafter for conciseness.

The optical receiver 20 and the optical receiver 11 may be configured to receive reflected light of the light emitted from the optical emitters 12, 13, and/or 14 simultaneously.

For example, the optical emitter 12 may emit light (such as a first light or green light) during a first-time interval and the optical receiver 20 may receive the reflected light of the first light during the first-time interval to monitor the first light. In some arrangements, the optical receiver 11 and the optical emitter 20 may be collaboratively configured to monitor a biological parameter (such as pulse rate) of an object or a target during the first-time interval.

For example, the optical emitter 13 may emit light (such as a second light or red light) during a second-time interval and the optical receiver 11 may receive the reflected light of the second light during the second-time interval to monitor the second light. The optical emitter 14 may emit light (such as a third light or IR light) during a third-time interval and the optical receiver 11 may receive the reflected light of the third light during the third-time interval to monitor the third light. In some arrangements, the optical receiver 11, the optical emitter 13, and the optical emitter 14 may be collaboratively configured to monitor a biological parameter (such as oxygen saturation) of an object or a target during the second-time interval and the third-time interval.

Therefore, the first-time interval and the second-time interval may be at least partially overlapped. The first-time interval and the third-time interval may be at least partially overlapped. The number and the locations of the optical receivers may be adjusted according to design requirements and are not intended to limit the present disclosure.

Figure 3:
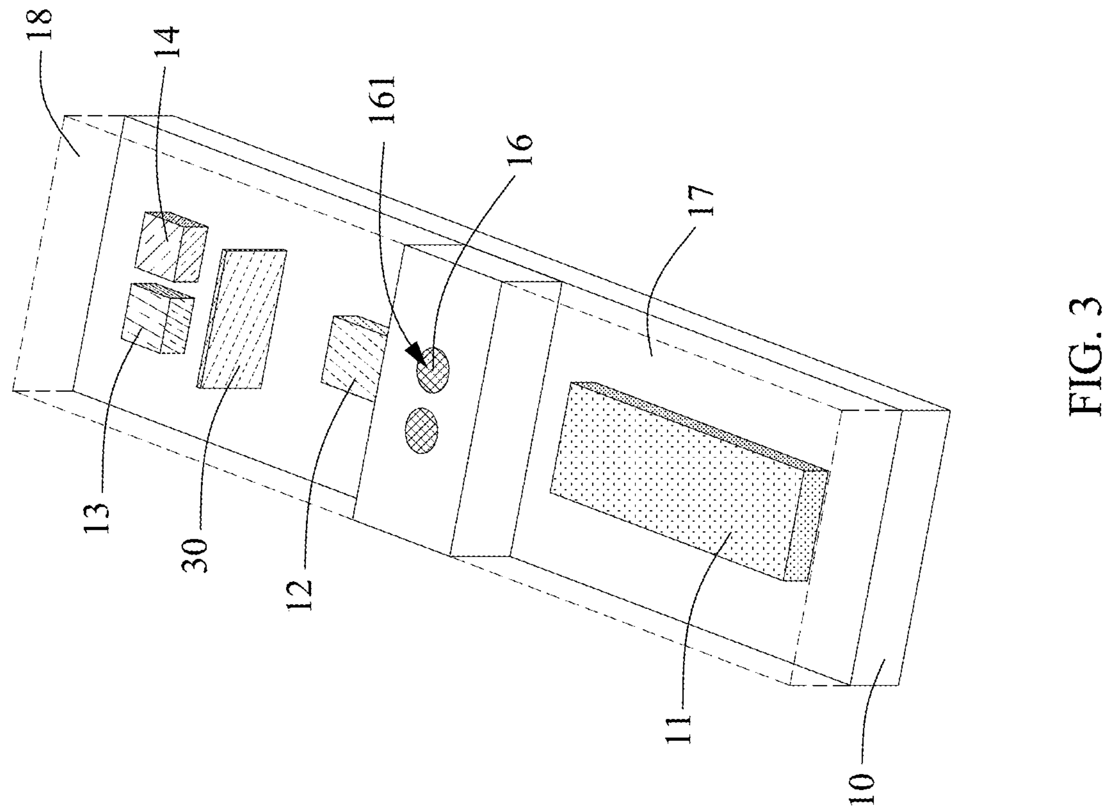
FIG. 3 illustrates a perspective view of an example of an optical module according to some arrangements of the present disclosure.

FIG. 3 illustrates a perspective view of an example of an optical module 3 according to some arrangements of the present disclosure. The optical module 3 is similar to the optical module 1 in FIG. 1A except for the differences described as follows.

The optical module 3 includes a light blocking structure 30. The light blocking structure 30 may be similar to the light blocking structure 15 of FIG. 1A. Therefore, some details of the light blocking structure 30 may correspond to the paragraphs described above for FIG. 1A, and a description thereof is not repeated hereinafter for conciseness.

The light blocking structure 30 may be disposed between the optical emitter 12 and one of the optical emitters 13 and 14. The light blocking structure 30 may be covered or encapsulated by the encapsulant 18.

The light blocking structure 30 may be non-transmissive to the light emitted from the optical emitters 12, 13, and/or 14. The light blocking structure 30 may be configured to block, reflect, scatter, or absorb light emitted from the optical emitters 12, 13, and/or 14. Therefore, crosstalk between light of different wavelengths (or frequencies, or bandwidths) can be decreased and the signal-to-noise ratio (SNR) of the optical module 3 can be further increased.

The number and the locations of the light blocking structures may be adjusted according to design requirements and are not intended to limit the present disclosure.

Figure 4:
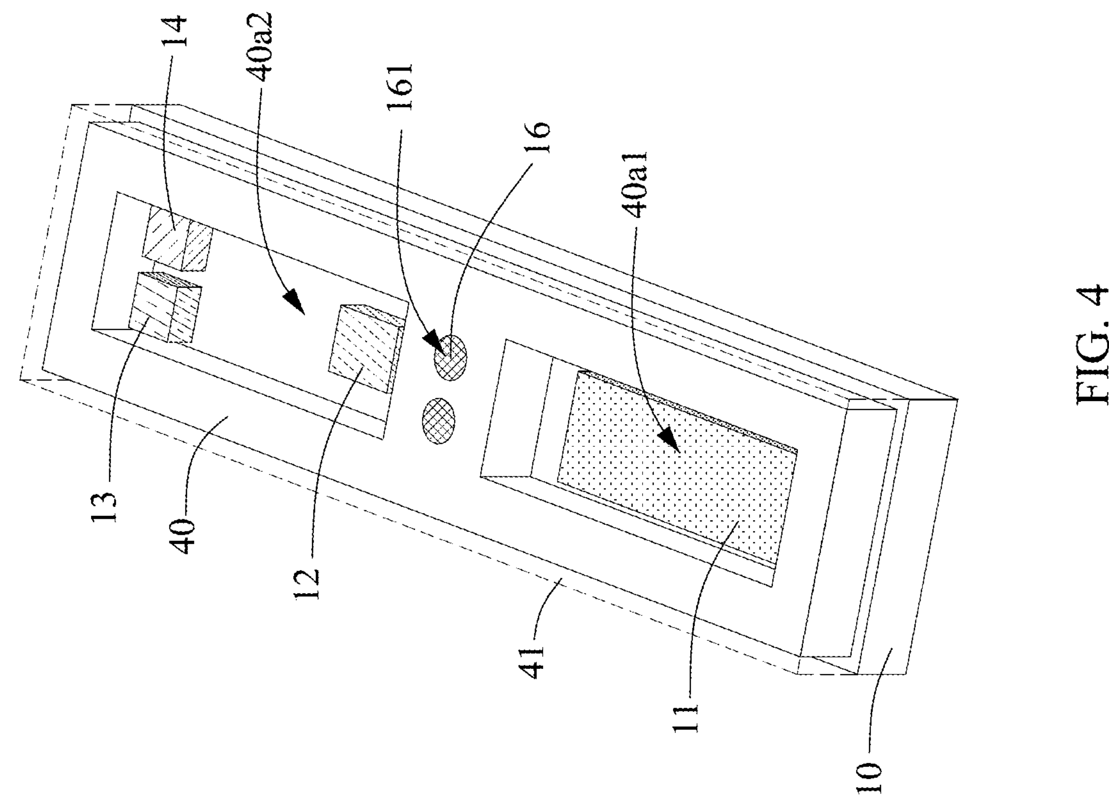
FIG. 4 illustrates a perspective view of an example of an optical module according to some arrangements of the present disclosure.

FIG. 4 illustrates a perspective view of an example of an optical module 4 according to some arrangements of the present disclosure. The optical module 4 is similar to the optical module 1 in FIG. 1A except for the differences described as follows.

The optical module 4 includes a light blocking structure 40 and an encapsulant 41. The light blocking structure 40 and the encapsulant 41 may be similar to the light blocking structure 15 and the encapsulant 17 (or the encapsulant 18), respectively, of FIG. 1A. Therefore, some details of the light blocking structure 40 and the encapsulant 41 may correspond to the paragraphs described above for FIG. 1A, and a description thereof is not repeated hereinafter for conciseness.

The light blocking structure 40 may surround the optical receiver 11, and the optical emitters 12, 13, and 14. The light blocking structure 40 may be disposed adjacent to the optical receiver 11. The light blocking structure 40 may be disposed adjacent to the optical emitters 12, 13, and 14. The light blocking structure 40 may define an aperture (or a receiving channel or aperture) 40*al* over the optical receiver 11. The light blocking structure 40 may define an aperture (or an emitting channel or aperture) 40*a*2 over the optical emitters 12, 13, and 14. The lateral surfaces of the light blocking structure 40 may be covered by the encapsulant 41.

In some arrangements, the light blocking structure 40 may be configured to prevent undesired light (e.g., light from an external environment) from being inadvertently detected by the optical receiver 11.

In some arrangements where the light blocking structure 40 is conductive, the entirety of the light blocking structure 40 may be an electrode and the sensing area of the optical module 4 may be increased.

The encapsulant 41 may each include a light transmissive material, such as clear glass, clear plastic, clear gel, clear resin, clear epoxy, sapphire, or other transparent materials. The encapsulant 41 may be disposed in the aperture 40*al* and the aperture 40*a*2.

Figure 5:
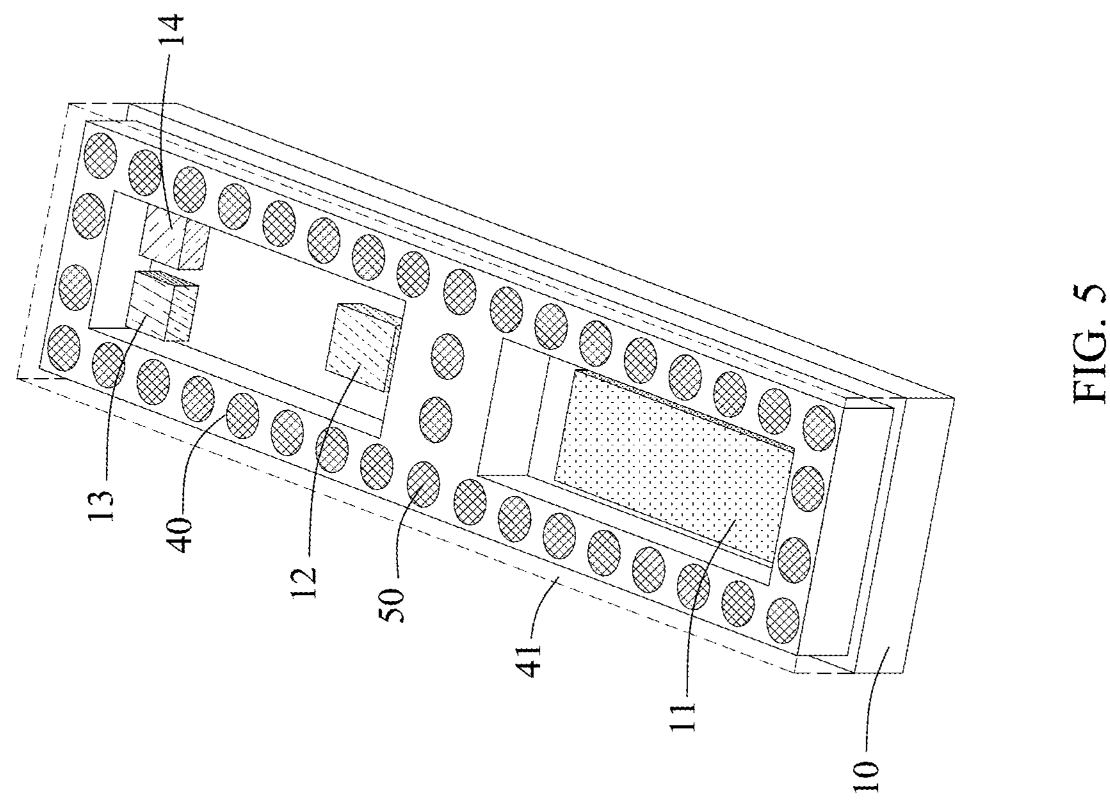
FIG. 5 illustrates a perspective view of an example of an optical module according to some arrangements of the present disclosure.

FIG. 5 illustrates a perspective view of an example of an optical module 5 according to some arrangements of the present disclosure. The optical module 5 is similar to the optical module 4 in FIG. 4 except for the differences described as follows.

The optical module 5 includes multiple conductive elements 50. The conductive elements 50 may be similar to the conductive element 16 of FIG. 1A. Therefore, some details of the conductive element 50 may correspond to the paragraphs described above for FIG. 1A, and a description thereof is not repeated hereinafter for conciseness.

The top surfaces of the conductive elements 50 may be equally spaced from the top view. For example, the conductive elements 50 may be arranged over the carrier 10 by an equal spacing or interval. However, in some arrangements, the conductive elements 50 may be arranged over the carrier 10 randomly.

In some arrangements, the conductive elements 50 may have a relatively lower impedance than the light blocking structure 40. Therefore, the sensitivity of the optical module 5 can be enhanced and the sensing efficiency can be increased. In some arrangements, the conductive elements 50 may provide multiple sensing regions of the electrical sensing function (such as an ECG function) for the optical module 5. Therefore, it may be easier for the user to place different body parts thereon. The number and the locations of the conductive elements may be adjusted according to design requirements and are not intended to limit the present disclosure.

Figure 6A:
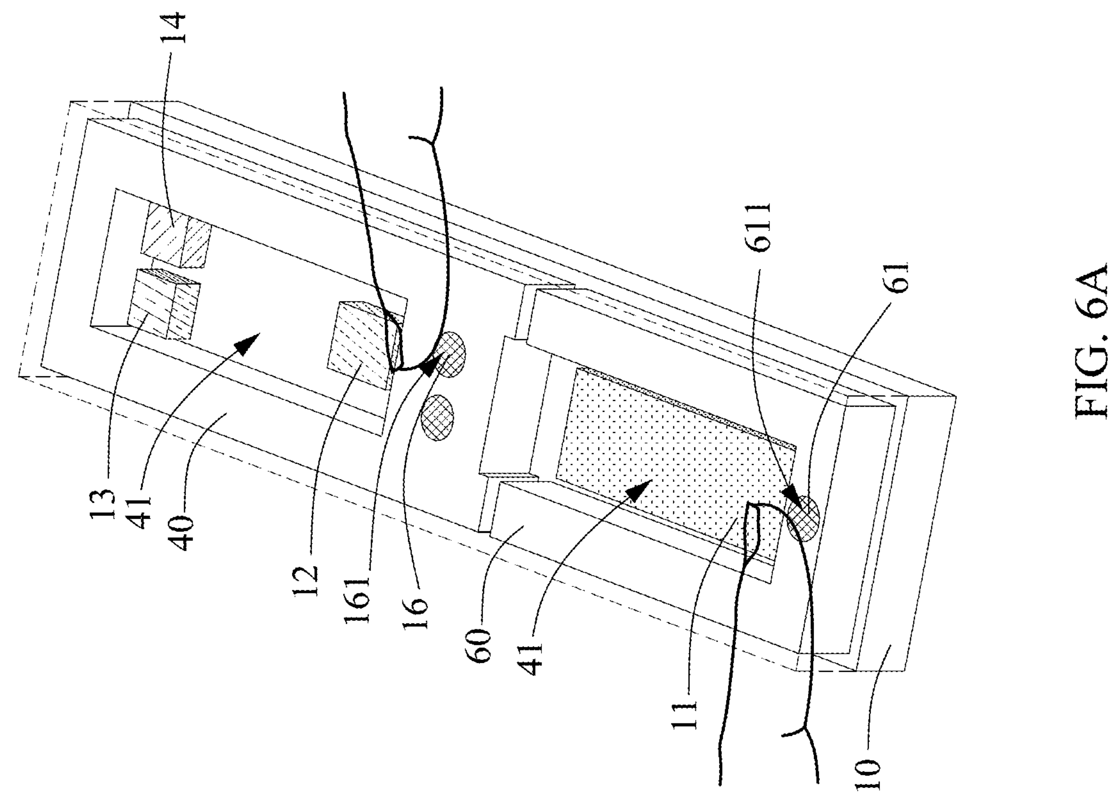
FIG. 6A illustrates a perspective view of an example of an optical module being used according to some arrangements of the present disclosure.
Figure 6B:
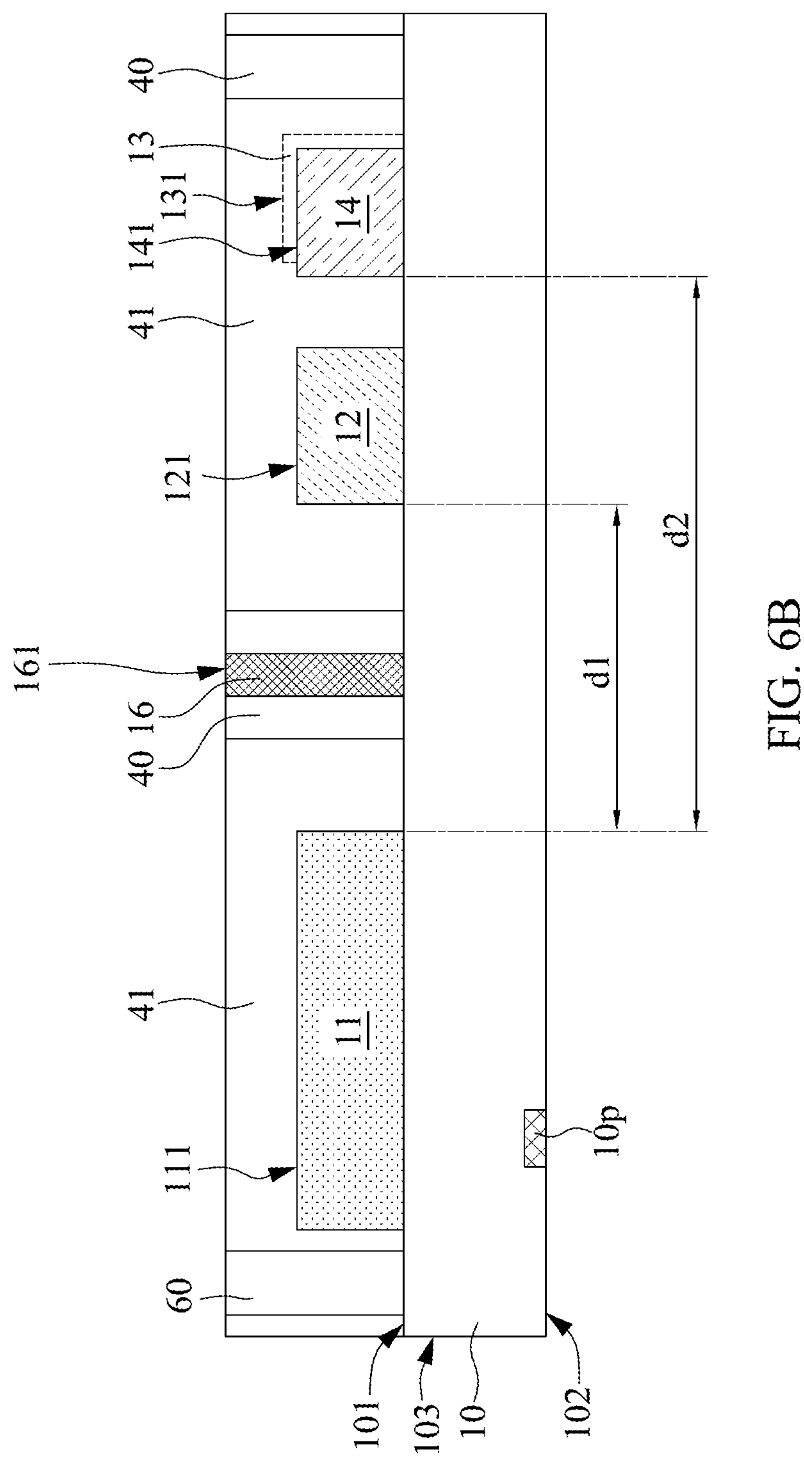
FIG. 6B illustrates a cross-sectional view of an example of an optical module according to some arrangements of the present disclosure.

FIG. 6A illustrates a perspective view of an example of an optical module 6 being used according to some arrangements of the present disclosure. FIG. 6B illustrates a cross-sectional view of an example of the optical module 6 according to some arrangements of the present disclosure. The optical module 6 is similar to the optical module 4 in FIG. 4 except for the differences described as follows.

The optical module 6 includes a light blocking structure 60 and a conductive element 61. The light blocking structure 60 and the conductive element 61 may be similar to the light blocking structure 15 and the conductive element 16, respectively, of FIG. 1A. Therefore, some details of the light blocking structure 60 and the conductive element 61 may correspond to the paragraphs described above for FIG. 1A, and a description thereof is not repeated hereinafter for conciseness.

The light blocking structure 60 may surround the optical receiver 11 and may be spaced apart from the light blocking structure 40. In some arrangements where the light blocking structure 60 and the light blocking structure 40 are conductive, the light blocking structure 60 and the light blocking structure 40 may be insulated from each other by the encapsulant 41.

In some arrangements where the light blocking structure 60 and the light blocking structure 40 are non-conductive, the light blocking structure 60 and the light blocking structure 40 may be connected to each other.

The conductive element 61 may be partially covered or encapsulated by the light blocking structure 60. A surface (such as a top surface) 611 of the conductive element 61 may be at least partially exposed from the light blocking structure 60.

In some embodiments, the conductive element 61 and the conductive element 16 may be used to form a part of a signal loop passing through a user's heart. For example, the conductive element 61 and the conductive element 16 may be used to form a part of an ECG lead. For example, the conductive element 61 may be a positive electrode and the conductive element 16 may be a negative electrode. For example, the conductive element 61 may be touched by the left-hand finger and the conductive element 16 may be touched by the right-hand finger. The locations of the electrodes may be designed to make it easier for the user to place them on different body parts.

Figure 7:
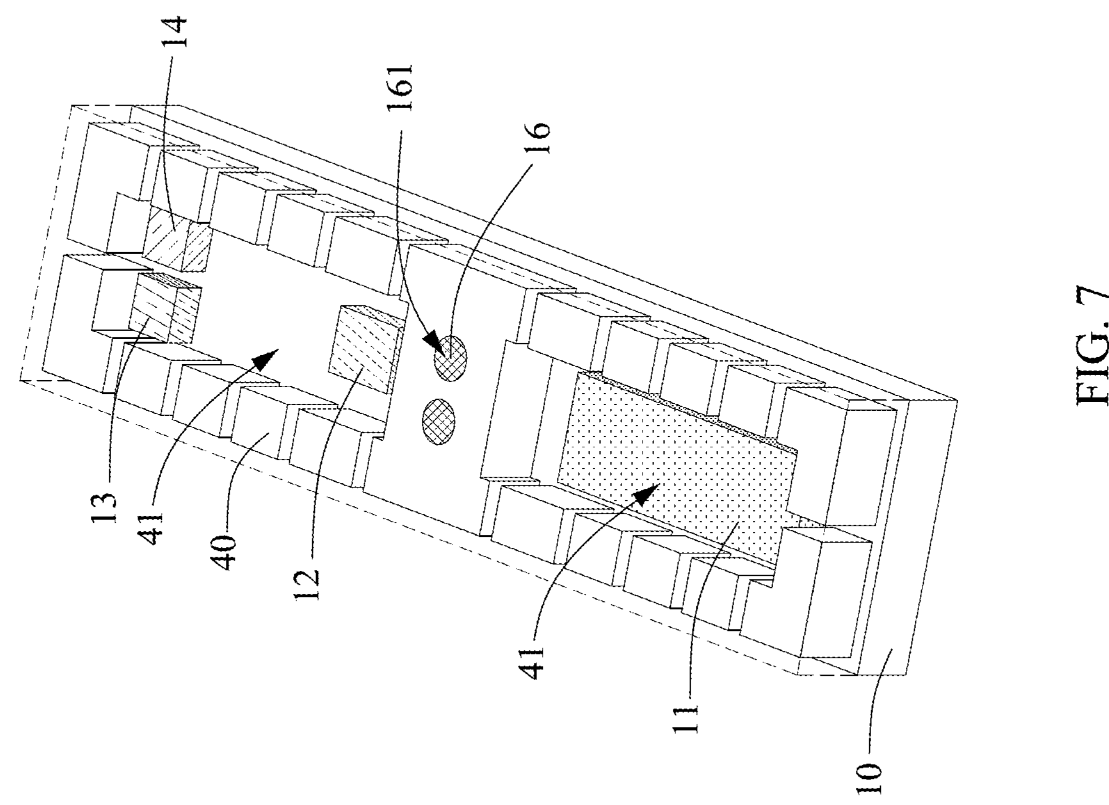
FIG. 7 illustrates a perspective view of an example of an optical module according to some arrangements of the present disclosure.

FIG. 7 illustrates a perspective view of an example of an optical module 7 according to some arrangements of the present disclosure. The optical module 7 is similar to the optical module 4 in FIG. 4 except that the light blocking structure 40 includes multiple segments or portions separated from one another.

In some arrangements, the number, patterns, locations of segments of the light blocking structure 40 may be adjusted according to design requirements and are not intended to limit the present disclosure. In some arrangements, one or more of the segments of the light blocking structure 40 may be conductive. In some arrangements, one or more of the segments of the light blocking structure 40 may be non-conductive. The conductive segments and the non-conductive segments may be arranged in a staggered or interval manner.

Figure 8A:
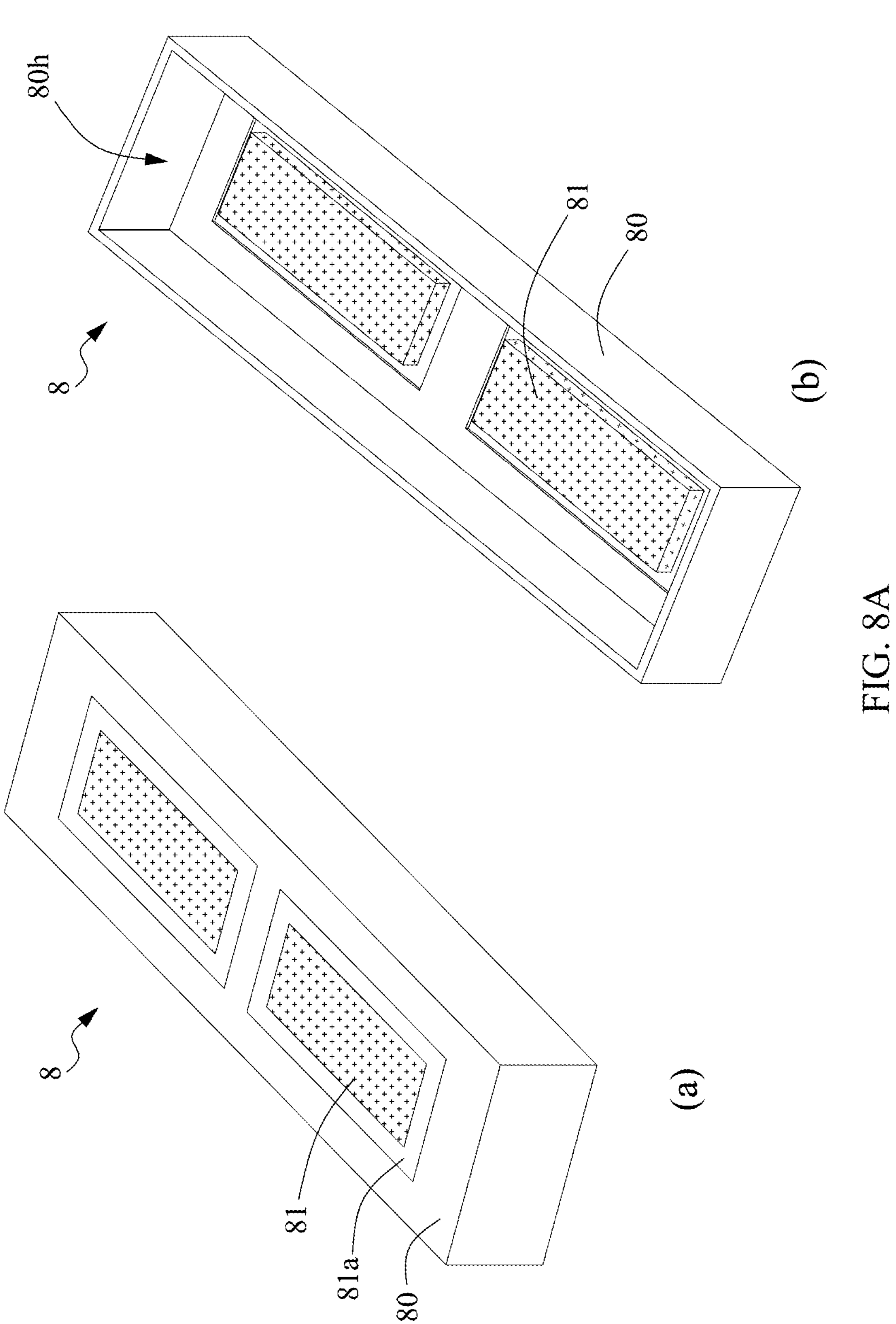
FIG. 8A illustrates perspective views of an example of a housing according to some arrangements of the present disclosure.

FIG. 8A illustrates perspective views of an example of a housing 8 according to some arrangements of the present disclosure.

The housing 8 may include a frame 80 and one or more of optical components 81. The frame 80 may include a plastic, a metal, a ceramic, or other suitable materials.

The optical component 81 may be transmissive to the light emitted from the optical emitters 12, 13, and 14 described above. The optical component 81 may include a light transmissive material, such as clear glass, clear plastic, clear gel, clear resin, clear epoxy, sapphire, or other transparent materials. In some arrangements, the optical component 81 may include a panel, a waveguide, a prism, a concave lens, a convex lens, a flat surface, a diffuser, a shutter, a filter, a holographic element, or another transparent element. In some arrangements, the optical component 81 may include or may be a glass portion of a portable electronic device or a wearable device. In some arrangements, the optical component 81 may be attached to the frame 80 by an adhesive layer 81*a*. The housing 8 may include an opening 80*h* for accommodating any one of the optical modules 1 through 7 described above.

Figure 8B:
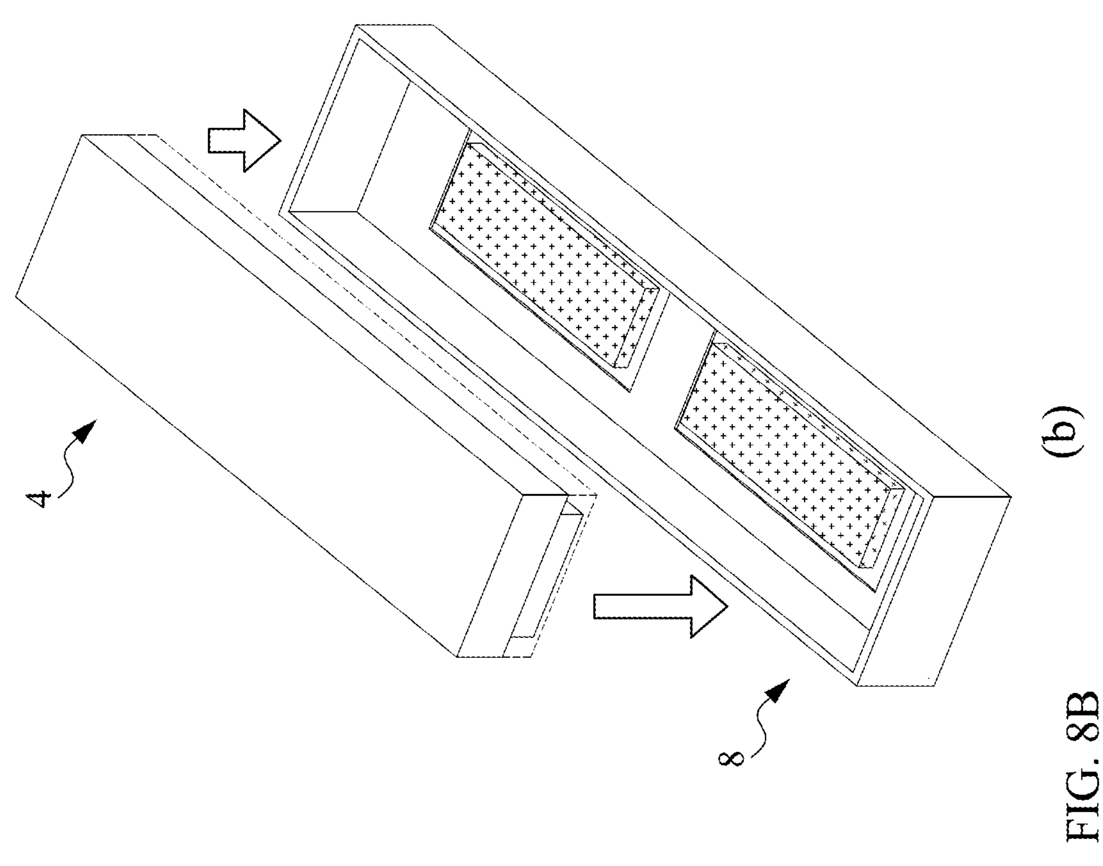
FIG. 8B illustrates perspective views of an example of a housing and an optical module according to some arrangements of the present disclosure.
Figure 8B:
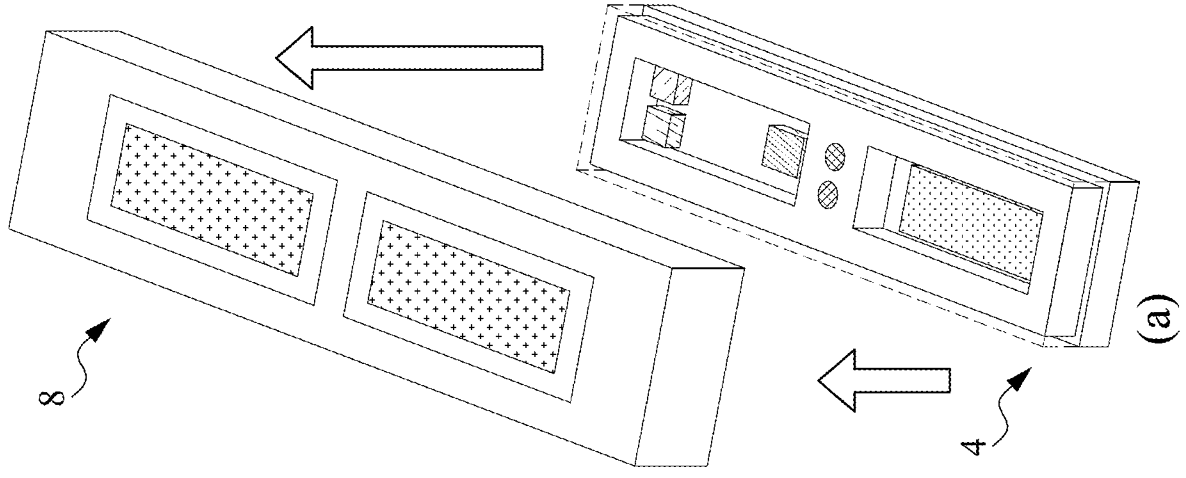
Figure 8C:
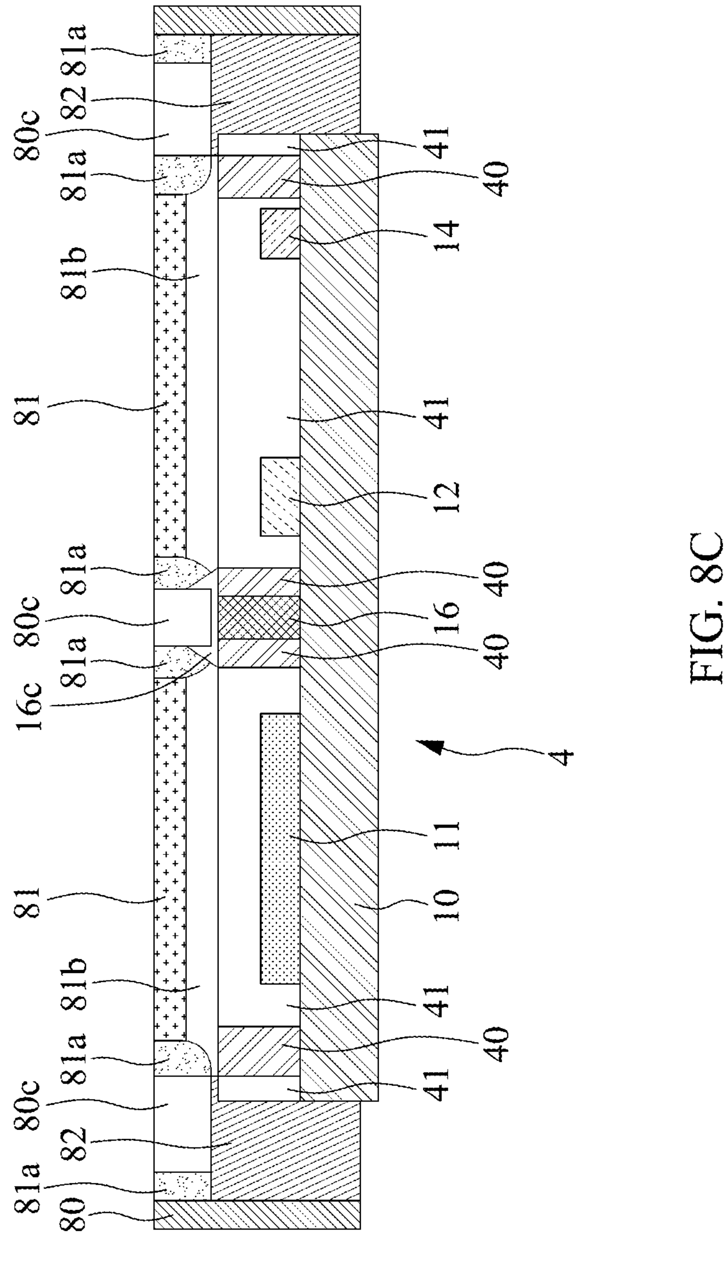
FIG. 8C illustrates a cross-sectional view of an example of a housing and an optical module according to some arrangements of the present disclosure.

FIG. 8B illustrates perspective views of an example of the housing 8 and the optical module 4 according to some arrangements of the present disclosure. FIG. 8C illustrates a cross-sectional view of an example of the housing 8 and the optical module 4 according to some arrangements of the present disclosure. In some arrangements, the structure in FIG. 8B may have a cross-sectional view as shown in FIG. 8C.

In some arrangements, the encapsulant 41 may be attached to the optical component 81 by an adhesive layer 81*b*. The adhesive layer 81*b* may be of the same material as the optical component 81, the encapsulant 41, or an index-matching material, which reduces the difference in refraction index (for the bandwidths of the optical emitters 12, 13, and 14) between the optical component 81 and the encapsulant 41.

In some arrangements, an encapsulant 82 may fill in the gap between the housing 8 and the optical module 4. In some embodiments, the encapsulant 82 may include an epoxy resin having fillers, a molding compound (e.g., an epoxy molding compound or other molding compound), a polyimide, a phenolic compound or material, a material with a silicone dispersed therein, or a combination thereof. In some embodiments, the encapsulant 82 may include an opaque material. In some embodiments, the opaque material may be an opaque epoxy (e.g., a black epoxy) or other opaque resin or polymer.

In some arrangements, the housing 8 may include one or more conductive regions 80*c* to increase the sensing region of the electrical sensing function (such as an ECG function) for the optical module 4. For example, a surface area of at least one of the conductive regions 80*c* may be greater than a surface area of the surface 161 of the conductive element 16.

For example, the at least one of the conductive regions 80*c* may be configured to face or contact an object (such as a user) of the optical module 4. The at least one of the conductive regions 80*c* may be electrically connected with the conductive element 16 through a conductive glue 16*c*. In some arrangements, the conductive glue 16*c* may be electrically connected with the conductive element 16 and the conductive regions 80*c*. The user may press the at least one of the conductive regions 80*c* against a first part of their body and press another electrode (such as the conductive element 10*p* in FIG. 1B) against a second part of their body.

Spatial descriptions, such as "above," "below," "up." "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of arrangements of this disclosure are not deviated from by such an arrangement.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to +10% of that numerical value, such as less than or equal to +5%, less than or equal to +4%, less than or equal to +3%, less than or equal to +2%, less than or equal to +1%, less than or equal to =0.5%, less than or equal to +0.1%, or less than or equal to +0.05%. For example, two numerical values can be deemed to be "substantially" the same or equal if a difference between the values is less than or equal to +10% of an average of the values, such as less than or equal to +5%, less than or equal to +4%, less than or equal to +3%, less than or equal to #2%, less than or equal to +1%, less than or equal to +0.5%, less than or equal to #0.1%, or less than or equal to +0.05%.

Two surfaces can be deemed to be coplanar or substantially coplanar if a displacement between the two surfaces is no greater than 5 μm, no greater than 2 μm, no greater than 1 μm, or no greater than 0.5 μm.

As used herein, the singular terms "a," "an," and "the" may include plural referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately 10+S/m, such as at least 105 S/m or at least 106 S/m. The electrical conductivity of a material can sometimes vary with temperature. Unless otherwise specified, the electrical conductivity of a material is measured at room temperature.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific arrangements thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other arrangements of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. An optical module, comprising:
a carrier having a first surface and a second surface opposite to the first surface;
a first optical receiver disposed over the second surface of the carrier;
a first optical emitter disposed over the second surface of the carrier;
an encapsulant covering the first optical receiver;
a first light blocking structure disposed over the second surface of the carrier and between the first optical receiver and the first optical emitter;
a first conductive element penetrating the first light blocking structure and having a surface exposed from the first light blocking structure; and
an electrode exposed from the first surface of the carrier and configured to collect an electrical signal associated with a user of the optical module, thereby providing an ECG function with the first conductive element,
wherein the encapsulant, the first light blocking structure, and the first conductive element defining a sensing surface facing away from the carrier,
wherein the sensing surface includes a transmissive region and a non-transmissive region adjacent to the transmissive region.

2. The optical module of claim 1, wherein the electrode has three surfaces embedded within the carrier.

3. The optical module of claim 2, wherein the electrode further has another surface substantially coplanar with the first surface of the carrier.

4. The optical module of claim 3, wherein the electrode and the conductive element are disposed on opposite sides of the carrier.

5. The optical module of claim 1, wherein the first conductive element functions as a button and is configured to spring back into shape after being pressed.

6. The optical module of claim 1, wherein the encapsulant, the first light blocking structure, and the conductive element are formed of different materials, and the sensing surface is substantially coplanar.

7. The optical module of claim 1, further comprising:
a second optical emitter disposed over the carrier; and
a third optical emitter disposed over the carrier, wherein the second optical emitter and the third optical emitter are disposed at substantially a same distance from the first optical receiver, wherein the first optical emitter is configured to emit a green light, the second optical emitter is configured to emit a red light, and the third optical emitter is configured to emit infrared (IR) light.

8. The optical module of claim 7, wherein the first optical emitter is closer to the first optical receiver than the second optical emitter and the third optical emitter.

9. The optical module of claim 8, further comprising:
a second light blocking structure separating the first optical emitter from the second optical emitter and the third optical emitter.

10. The optical module of claim 7, wherein the first optical emitter, the second optical emitter, and the third optical emitter are configured to emit the green light, the red light, and the IR light simultaneously, and the first optical receiver includes different light receiving regions for receiving reflected lights of the green light, the red light, and the IR light simultaneously.

11. The optical module of claim 7, wherein the first optical receiver is configured to monitor reflected lights of the green light, the red light, and the IR light by a same light receiving region during different time intervals.

12. The optical module of claim 7, further comprising:
a second optical receiver disposed over the carrier, wherein the first optical receiver and the second optical receiver are configured to monitor reflected lights of the green light, the red light, and the IR light during different time intervals.

13. The optical module of claim 1, wherein the first light blocking structure surrounds the first optical receiver on four sides, and surrounds the first optical emitter on four sides, and wherein the first light blocking structure defines an aperture in which the first optical receiver is disposed, and wherein the encapsulant covers an internal surface and an external surface of the aperture.

14. The optical module of claim 1, further comprising:
a housing having a conductive region electrically connected to the conductive element through a conductive glue, wherein the conductive region and the conductive element are overlapped in a direction substantially perpendicular to the second surface of the carrier.

15. The optical module of claim 1, further comprising:
a plurality of conductive elements penetrating the first light blocking structure, wherein the plurality of conductive elements are arranged in a line.

16. The optical module of claim 1, further comprising:
a second light blocking structure disposed over the carrier and surrounds the first optical receiver on three sides, wherein the first light blocking structure surrounds the first optical emitter on four sides, and wherein the second light blocking structure is spaced apart from the first light blocking structure.

17. The optical module of claim 16, further comprising:
a second conductive element penetrating the second light blocking structure and having a surface exposed from the second light blocking structure, wherein the second conductive element functions as a positive electrode and the first conductive element functions as a negative electrode.

18. An optical module, comprising:
a carrier;
an optical receiver disposed over the carrier:
an optical emitter disposed over the carrier;
an encapsulant covering the optical receiver:
a light blocking structure disposed over the carrier and between the optical receiver and the optical emitter; and
a conductive element penetrating the light blocking structure and having a surface exposed from the light blocking structure; and
wherein the encapsulant, the light blocking structure, and the conductive element defining a sensing surface facing away from the carrier,
wherein the sensing surface includes a transmissive region and a non-transmissive region adjacent to the transmissive region,
a housing having a conductive region electrically connected to the conductive element through a conductive glue, wherein the conductive region and the conductive element are overlapped in a direction substantially perpendicular to a surface of the carrier.

19. The optical module of claim 18, wherein a surface area of the conductive region is greater than the surface of the conductive element.

* * * * *